United States Patent [19]
Gerstel et al.

[11] Patent Number: 5,588,988
[45] Date of Patent: Dec. 31, 1996

[54] THERMAL DESORPTION DEVICE FOR A GAS CHROMATOGRAPH

[76] Inventors: Eberhard Gerstel, An der Halde 49, 45475 Mulheim/Ruhr; Ralf Bremer, Witthausstr. 29, 45470 Mulheim/Ruhr, both of Germany

[21] Appl. No.: 461,869

[22] Filed: Jun. 5, 1995

[30] Foreign Application Priority Data

Jun. 3, 1994 [DE] Germany ............ 44 19 596.6

[51] Int. Cl.$^6$ ................................................. B01D 15/08
[52] U.S. Cl. ....................... 96/101; 96/103; 96/105; 73/23.41
[58] Field of Search .................. 73/19.02, 23.35, 73/23.41; 96/101–107

[56] References Cited

U.S. PATENT DOCUMENTS

| | | | |
|---|---|---|---|
| 3,063,286 | 11/1962 | Nerheim ........................... | 96/105 X |
| 4,180,389 | 12/1979 | Paul ................................. | 96/101 X |
| 4,699,768 | 10/1987 | Weiss ............................... | 96/101 X |
| 5,109,710 | 5/1992 | Newkirk et al. ................... | 73/23.41 X |
| 5,288,310 | 2/1994 | Peters et al. ...................... | 96/104 |
| 5,402,668 | 4/1995 | Murakami et al. ................. | 73/19.02 |

FOREIGN PATENT DOCUMENTS 451566 10/1991 European Pat. Off. .

*Primary Examiner*—Robert Spitzer
*Attorney, Agent, or Firm*—Steven F. Caserza; Flehr, Hohbach, Test, Albritton & Herbert

[57] ABSTRACT

The invention relates to a thermal desorption device for a gas chromatograph, having a thermostatically controlled oven (1) provided with a carrier gas connection and having an evaporator tube. In this case, the evaporator tube is an interchangeable sample holder tube (5) which can be held by a holding chamber (2) in the oven (1), which sample holder tube can be fitted into a holder piece (6) with one end externally sealed by a seal (8), the holder piece (6) having two seals (9) arranged separated in the region of its casing and being capable of being fitted into a correspondingly designed holder (10), the carrier gas connection (14) opening in the region (12) of an annular gap (13) between the holder (10) and the holder piece (6) between the two seals (9) located on the casing, which annular gap (13) is, for its part, connected to an annular gap (15) surrounding the inserted end of the sample holder tube (5), a trap (18) being connected downstream.

11 Claims, 1 Drawing Sheet

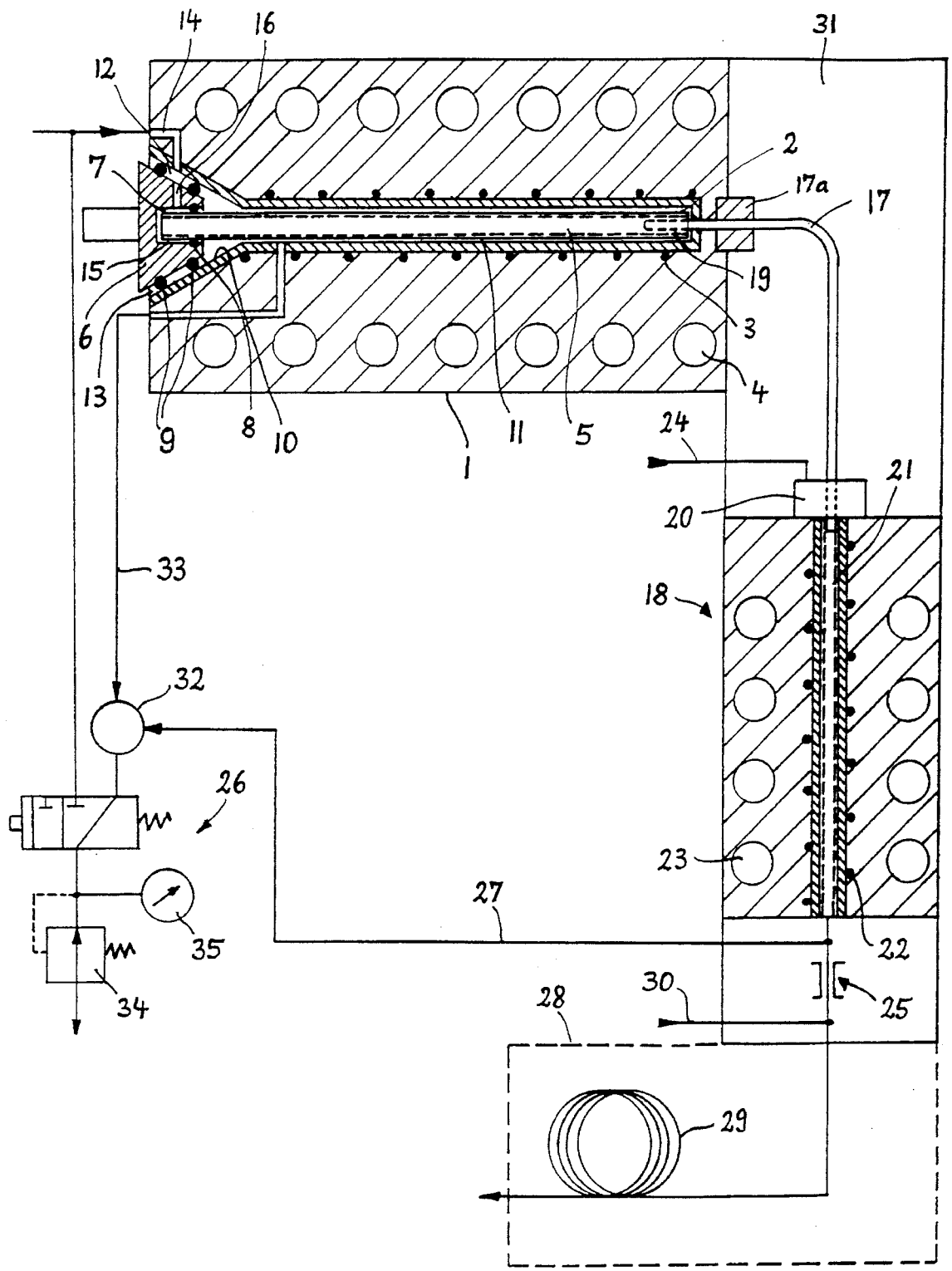

THERMAL DESORPTION DEVICE FOR A GAS CHROMATOGRAPH

TECHNICAL FIELD

The invention relates thermal desorption device for a gas chromatograph.

BACKGROUND OF THE INVENTION

EP-A-0,451,566 discloses a gas chromatography device having a sample delivery device which comprises an evaporator tube, which can be subjected to cooling and regulated heating, for retaining or releasing, thermal desorption, delivered sample material, which evaporator tube can be exposed to the action of a carrier gas stream from a corresponding gas source and is followed by a separation column. In this case, a regulated carrier gas stream is fed through the sample delivery device, delivery of the liquid sample material, consisting of solvent and substances to be examined, taking place in a first operating state, while access to the separation column is pneumatically blocked by a regulated auxiliary gas stream, and the carrier gas stream together with the solvent is discharged through an open discharge line and substances to be examined are retained in an evaporator tube located in front of the separation column. In a second operating state, in which the discharge line for the carrier gas stream is closed and the auxiliary gas stream is interrupted, the substances of the sample material which were retained during the first operating state are fed to the separation column by heating the evaporator tube. This is, however, suitable only for liquid samples and not for solid samples or gaseous samples adsorbed onto solid substances.

DISCLOSURE OF THE INVENTION

The object of the invention is to provide a thermal desorption device which is of simple construction and makes possible simple, problem-free sample delivery for examining solid sample material or liquid or gaseous sample material adsorbed onto solid substances.

This object is achieved according to the features of claim 1.

The thermal desorption device is, for example, suitable for delivering substances thermally desorbed directly from solid materials, such as contaminated soils, plastics, synthetic fibers, coffee, tea, spices etc. or for examining trace components in general from gaseous samples, extracted air, room air, exhaust gases, for example for checking that prescribed limit values have been adhered to. A sample holder tube is simply filled with the sample material, inserted by one end into a holder piece and then fitted together with the holder piece into the device. No particular sample preparation is necessary and a multiplicity of sample holder tubes can be fitted without problems one after the other, and even automatically.

Further refinements of the invention are described hereinbelow and can be found in the subclaims.

The invention is explained in more detail below with the aid of an exemplary embodiment schematically represented in the enclosed drawing.

The represented thermal desorption device for a gas chromatograph comprises an oven 1 which can be subjected to cooling and regulated heating and which has an inner holder chamber 2, which, on the one hand, is surrounded by a heating device 3 for regulated heating of the holder chamber 2 and, on the other hand, is surrounded by coolant bores 4 which are connected to a coolant source, for example a source of liquid nitrogen.

The holder chamber 2 is used for interchangeable holding of a sample holder tube 5 which is used for holding sample material to be examined. The sample material with which the sample holder tube 5 is filled may be solid materials containing volatile components, such as, for example, powder, granules, soils or the like, or volatile or semivolatile substances which are adsorbed onto an adsorbent.

A holder piece 6 which has an axially central blind bore 7 provided in the vicinity of its opening with a groove holding an O-ring 8 is provided for the sample holder tube 5. The holder piece 6 is conically designed on the outside and is provided with two grooves arranged separated on its conical casing, each of which grooves holds an O-ring 9. The blind bore 7 interchangeably holds one end of the sample holder tube 5.

The holder chamber 2 has, on its externally open end, a frustoconical holder 10 for the holder piece 6 and forms an annular gap 11 with the sample holder tube 5. When the holder piece 6 is fitted, the O-rings 9 seal off a section 12 of an annular gap 13 between the holder piece 6 and the holder 10, into which annular gap a carrier gas line 14 opens. The region, sealed off by the O-ring 8 toward the holder chamber 2, of an annular gap 15 surrounding the sample holder tube 5 in the blind bore 7 is connected via a bore 16 to the section 12 of the annular gap 13 and thereby to the carrier gas line 14, so that the carrier gas fed via the carrier gas line 14 can flow into the sample holder tube 5.

A transfer capillary 17 which leads to a trap 18 opens into the holder chamber 2. The transfer capillary 17 projects to some extent into the holder chamber 2, so that it is held to this extent, when the sample holder tube 5 is fitted, by the latter to form an annular gap 19. A sample delivery device as is described in EP-A-0,451,566 is, for example, suitable as the trap 18. This device comprises a head 20 with an evaporator tube 21 arranged therein, which evaporator tube can be subjected to cooling and regulated heating by means of a corresponding cooling device 22 and a corresponding heating device 23. A temperature sensor, not shown, and a regulator which is not shown and, if appropriate, also controls the regulated heating of the oven I by means of a corresponding temperature sensor, is provided for this purpose. Carrier gas can be fed to the evaporator tube 21 via the carrier gas line 14. It is, however, also possible to provide a separate carrier gas line 24, via which carrier gas is fed on the inlet side to the evaporator tube 21. The carrier gas may originate from the same source as that for the carrier gas line 14 and may likewise have its flow regulated. The use of a separate carrier gas line 24 allows pneumatic decoupling of the oven 1.

The evaporator tube 21 may be unfilled and provided with recesses for forming turbulence or may be filled with an adsorbent such as glass wool or may be provided with an internal coating or may be filled with an adsorbent dependent on the application.

At the outlet end of the evaporator tube 21 there is a throttle 25, in front of which a gas discharge line 27 provided with a valve device 26 branches off, while the exit of the throttle leads to a gas chromatography capillary column 29 located in an oven 28. The throttle 25 can be closed off pneumatically by means of a carrier gas feed line 30 opening at the outlet side thereof.

The transfer capillary 17 is arranged in a transfer space 31 which thermally conditions it and extends from the oven 1 to the head 20, in order to avoid material losses by condensation.

After a sample holder tube 5 has been filled with the sample material, it is closed off on both sides with a gas-permeable plug, inserted by one end into the holder piece 6 and then fitted together with the latter into the holder chamber 2. The holder piece 6 is expediently axially braced and secured, with respect to the holder 10, on the oven 1 using means, not shown, in order to guarantee sealing engagement of the O-rings 9 with the conical surface of the holder 10.

The carrier gas supply is then turned on, so that carrier gas is fed through the sample holder tube 5, via the transfer capillary 17 into the trap 18. The oven 1 is simultaneously heated up in regulated fashion from its initial temperature to a maximum temperature which, for example, may be 350° C. The heating device 3 is in this case designed such that a temperature gradient results which increases from the side of the holder piece 6 to the central region of the sample holder tube 5, and is constant from there to the transfer capillary 17. In this case the temperature at the holder piece 6 should be low enough for the elastomer material of the O-ring 8 not to make a contribution through degassing. In the case of manual assembly, it is thereby also possible to take hold of the holder piece 6. An adapter 17a made of a material with high thermal conductivity, such as silver, may be provided toward the transfer capillary 17.

In this case, the throttle 25 is pneumatically closed and the gas discharge line 27 is opened.

The thermally desorbed substances enter the trap 18 which is, for example, cooled to a temperature in the range of −50° to −150° C. and are then retained there. When the maximum temperature of the oven 1 is reached and has been maintained for the desired period of time, the thermal desorption is turned off by cooling the sample holder tube 5 to the initial temperature by means of the coolant. The evaporator tube 21 is then heated up in regulated fashion, so that the substances retained therein are thermally desorbed according to the respective temperature.

Depending on whether the working step is operated with or without splitting, the throttle 25 remains pneumatically closed and the gas discharge line 27 open at first, or the throttle 25 and therefore the access to the capillary column 29 is opened and the gas discharge line 27 is closed.

In the case of thermal desorption of the sample material too the operation may be carried out using splitting. For this purpose, the annular gap 11 is connected to a gas discharge line 33 connected to a 2-way solenoid valve 32, the gas discharge line 27 opening at one inlet of the solenoid valve 32. When splitting is employed, the outlet of the solenoid valve 32 is connected to the gas discharge line 33 during the thermal desorption in the oven 1, and is connected to the gas discharge line 27 during the thermal desorption in the evaporator tube 21. In this way it is possible to work selectively with single splitting in the oven 1 or in the evaporator tube 21 or with double splitting, in each of them. In the latter case, total splitting of 1:10,000 results from single splitting of 1:100 in each case.

After the thermal desorption in the oven 1 or in the trap 18, these components are cooled quickly by corresponding coolant supply, so that they are available for another sample.

The sample holder tube 5, the transfer capillary 17, the evaporator tube 21 and, if appropriate, the lining of the oven 1, which lining forms the holder chamber 2, may, like the parts following the evaporator tube 21, consist of glass or glassy material, or may be lined therewith, while the seals required between them are graphite seals, so that the thermally desorbed substances do not come into contact with metal.

The heating of the oven 1 or of the trap 18 can be carried out in programmed fashion depending on the sample, it being possible to use heating rates in, for example, the range of 1° to 60° C./min. The desorption time and desorption flux can correspondingly be set independently of each other.

In the exemplary embodiment represented, the carrier gas is also used between the individual thermal desorptions as a purge gas.

If appropriate, cooling of the oven 1 may likewise be carried out in regulated fashion, in order to make it possible to thermally desorb even at low temperatures, approximately room temperature or below.

The carrier gas supply via the carrier gas line 14 and, if appropriate, 24 expediently takes place using mass flow rate regulation, preferably carried out electronically, so that a constant carrier gas pressure is maintained. The valve device 26 may thus comprise a back-pressure regulator 34 and a manometer 35.

The holder piece 6 and the holder 10 may also be cylindrical, although the conical design is preferred.

What is claimed:

1. A thermal desorption device for a gas chromatograph comprising:

an oven;

a holding chamber having an open receiving portion;

an interchangeable sample holder tube, having a first end and a second end, receivable by said holding chamber;

a sample holder tube holder piece for engagement with said receiving portion of said holding chamber and having a proximal and a distal end, said distal end including a recess for placement of said first end of said sample holder tube;

a first seal near said proximal end of said holder piece, for externally sealing said holding chamber;

a second seal near said distal end of said holder piece;

a first annular gap located around that portion of said holder piece between said first and second seals;

a carrier gas connection opening in the region of said first annular gap;

a third seal in said recess surrounding said sample holder tube at a point near said distal end of said holder piece, forming a seal between said sample holder tube and said holder piece;

a second gap surrounding said first end of said sample holder tube up to said third seal;

a connection through said holder piece between said first and second gaps; and a trap communication with the interior of said sample holder tube at said second end.

2. The thermal desorption device as in claim 1, wherein said holder piece has a conical shape between said proximal end and said distal end which matches a conical shape of said receiving portion of said holding chamber.

3. The thermal desorption device as in claims 1 or 2, wherein said holder piece can be braced in said holding chamber.

4. The thermal desorption device as in claim 1, wherein a transfer capillary is arranged between said holding chamber and said trap.

5. The thermal desorption device as in claim 4, wherein the end of said transfer capillary projects into said sample holder tube when the latter is fitted.

6. The thermal desorption device as in claim 4, wherein said trap is designed in the form of an evaporator tube which can be subjected to cooling and regulated heating and is provided with a carrier gas connection, said transfer capillary being arranged in a transfer space thermally conditioning said transfer capillary.

7. The thermal desorption device as in claim 1, wherein said holding chamber is connected to a closeable gas discharge line.

8. The thermal desorption device as in claim 1, wherein said oven is thermostatically controlled with adjustable or programmed heating or cooling rate.

9. The thermal desorption device as in claims 1 or 8, wherein said trap is thermostatically controlled with adjustable or programmed heating or cooling rate.

10. The thermal desorption device as in claim 8 wherein said oven has a heating device which produces during heating a temperature gradient which falls toward said holder piece.

11. The thermal desorption device as in claim 1, wherein said sample holder tube comprises a glass tube.

* * * * *